(12) United States Patent
Mirsky et al.

(10) Patent No.: US 7,884,940 B2
(45) Date of Patent: Feb. 8, 2011

(54) DISTRIBUTED MEASUREMENT SPOTS AND REFERENCE SPOTS, ESPECIALLY FOR CHEMOSENSORS AND BIOSENSORS

(75) Inventors: Vladimir Mirsky, Sinzing (DE); Alex Mirsky, Sinzing (DE)

(73) Assignee: Mivitec GmbH, Sinzing (DE)

( * ) Notice: Subject to any disclaimer, the term of this patent is extended or adjusted under 35 U.S.C. 154(b) by 385 days.

(21) Appl. No.: 12/085,088

(22) PCT Filed: Nov. 16, 2006

(86) PCT No.: PCT/EP2006/011017

§ 371 (c)(1),
(2), (4) Date: May 15, 2008

(87) PCT Pub. No.: WO2007/057195

PCT Pub. Date: May 24, 2007

(65) Prior Publication Data

US 2009/0046292 A1    Feb. 19, 2009

(30) Foreign Application Priority Data

Nov. 16, 2005  (DE) ................. 10 2005 054 495

(51) Int. Cl.
*G01N 21/55* (2006.01)
(52) U.S. Cl. ........................ 356/445; 356/448
(58) Field of Classification Search ............ 356/244, 356/445–448
See application file for complete search history.

(56) References Cited

U.S. PATENT DOCUMENTS 6,458,600 B1   10/2002  Mirsky et al.

(Continued)

FOREIGN PATENT DOCUMENTS

DE         19829657 A1    4/1999

(Continued)

OTHER PUBLICATIONS

Alexander Zybin et al., "Double-Wavelength Technique for Surface Plasmon Resonance Measurements: Basic Concept and Applications for Single Sensors and Two-Dimensional Sensor Arrays", Analytical Chemistry, Apr. 15, 2005, pp. 2393-2399, vol. 77, No. 8.

(Continued)

*Primary Examiner*—Gregory J Toatley
*Assistant Examiner*—Tri T Ton
(74) *Attorney, Agent, or Firm*—Tim Tingkang Xia; Morris, Manning & Martin, LLP

(57) ABSTRACT

A sensor device has at least one array of sensor spots disposed on or in a common substrate or retained by a common substrate. At least one first group of several sensor spots of the array is configured as measurement spots which respond to at least one parameter to be measured, while at least one second group of several sensor spots of the array is configured as reference spots which do not respond or respond only insignificantly to the parameter to be measured. The reference spots are embodied in such a way relative to the associated measurement spots that the reference spots respond to at least one boundary condition variable to which the measurement spots respond as well and which influences the at least one test signal such that the reference signal directly or indirectly represents the boundary condition variable or a change in the boundary condition variable.

28 Claims, 7 Drawing Sheets

U.S. PATENT DOCUMENTS

2005/0017191 A1  1/2005  Montagu et al.

FOREIGN PATENT DOCUMENTS

| EP | 1617203 A1 | 3/2004 |
| EP | 1566627 A1 | 8/2005 |
| JP | 2004037103 | 2/2005 |
| WO | 0203142 A2 | 1/2002 |
| WO | 0246756 A1 | 6/2002 |

OTHER PUBLICATIONS

Vladmir M. Mirsky et al., "Capacitive Monitoring of Protein Immobilization and Antigen-Antibody Reactions on Monomolecular Alkylthiol Films on Gold Electrodes", Biosensors & Bioelectronics, 1997, pp. 977-989, vol. 12, No. 9-10, Elsevier Science Limited, Great Britain.

Nadia Wrobel et al., "Covalent Immobilization of Oligonucleotides on Electrodes", Colloids and Surfaces B: Biointerfaces 32, 2003, pp. 157-162, Science Direct, Elsevier.

Jiri Homola, "Surface Plasmon Resonance Based Sensors", Springer Series on Chemical Sensors and Biosensors, vol. 4, 2006.

Takuo Akimoto et al., "A Surface Plasmon Resonance Probe With a Novel Integrated Reference Sensor Surface", Biosensors & Bioelectronics 18, 2003, pp. 1447-1453, Science Direct, Elsevier. ET AL.

Anuj K. Sharma et al., "On the Sensitivity and Signal to Noise Ratio of a Step-Index Fiber Optic Surface Plasmon Resonance Sensor with Bimetallic Layers", Optics Communications 245, 2005, pp. 159-169, Science Direct Elsevier.

Charles E.H. Berger et al., "Differential SPR Immunosensing", Sensors and Actuators B 63, 2000, pp. 103-108, Elsevier.

Hongbo B. Lu et al., "Protein Contact Printing for a Surface Plasmon Resonance Biosensor with On-Chip Referencing", Sensors and Actuators B 74, 2001, pp. 91-99, Elsevier.

Stepan A. Zynio et al., "Bimetallic Layers Increase Sensitivity of Affinity Sensors Based on Surface Plasmon Resonance", Sensors, 2002, pp. 63-70, MDPI.

Joseph R. Lakowica, "Radiative Decay Engineering 3. Surface Plasmon-Coupled Directional Emission", Analytical Biochemistry 324, 2004, pp. 153-169, Science Direct, Elsevier.

Nidhi Nath et al., "A Colorimetric Gold Nanoparticle Sensor to Interrogate Biomolecular Interactions in Real Time on a Surface", Analytical Chemistry, 2002, pp. 504-509, vol. 74 No. 3.

Charles T. Campbell, "Surface Plasmon Resonance (SPR) Biosensor Development".

Alexander Zybin et al., "Double-Wavelength Technique for Surface Plasmon Resonance Measurements: Basic Concepts and Applications for Single Sensors and Two-Dimensional Sensor Arrays", Analytical Chemistry, 2005, p. 2396-2397, vol. 77 No. 8.

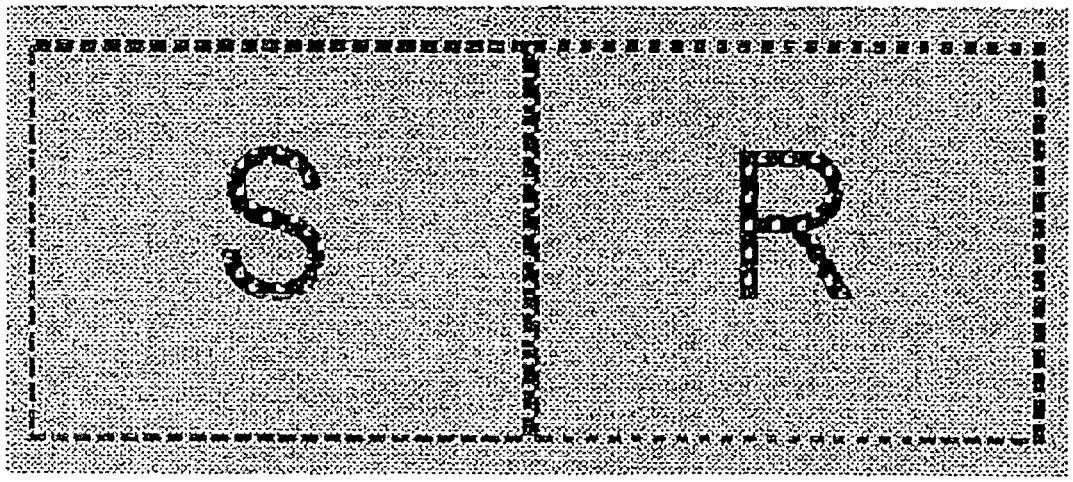
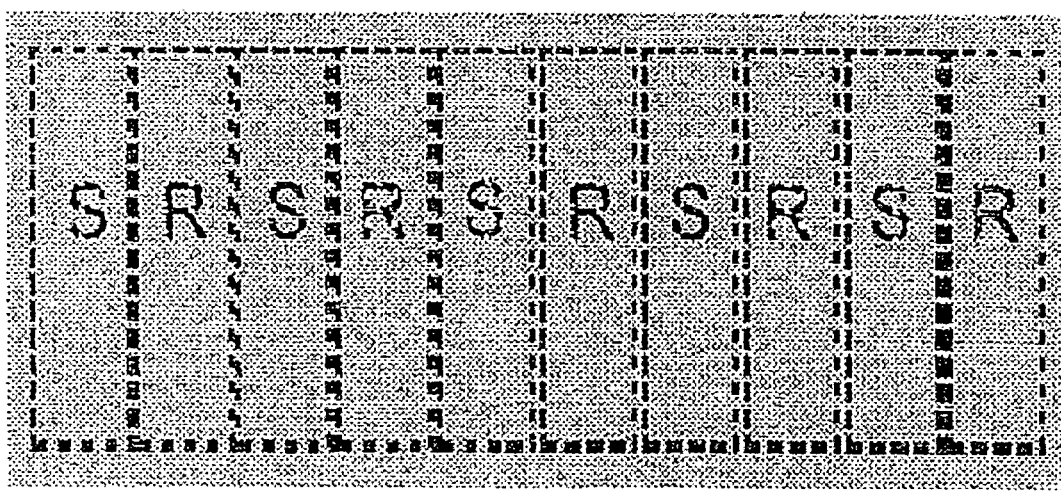
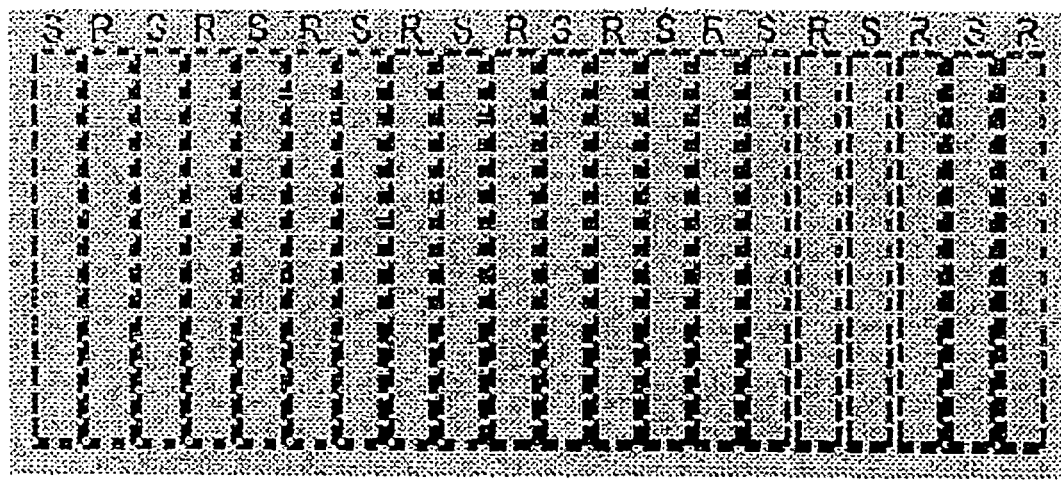
Fig. 46

DISTRIBUTED MEASUREMENT SPOTS AND REFERENCE SPOTS, ESPECIALLY FOR CHEMOSENSORS AND BIOSENSORS

FIELD OF THE INVENTION

The invention relates generally to measuring processes and measuring assemblies using at least two types of sensor spots, namely on the one hand measurement spots and on the other hand reference or calibration spots (referred to hereinafter generally only as reference spots), wherein a measuring signal obtained based on at least one measurement spot is further evaluated on the basis of a reference or calibration signal obtained based on at least one reference or calibration spot (referred to hereinafter generally only as a reference signal), in particular is corrected or calibrated with regard to certain influences and/or a differential measurement is carried out by means of the at least one measurement spot and the at least one reference or calibration spot. Examples include surface plasmon resonance (SPR) measurements which are carried out optically.

BACKGROUND OF THE INVENTION

With regard to the SPR measuring method which is particularly—but not exclusively—of interest in view of implementing the proposals of the invention, reference may for example be made, concerning the technical background, the metrological equipment and relevant applications, to: A. Zybin et al., *Anal. Chem.*, 2005, 77, 2393-2399; T. Akimoto et al., *Biosensors and Bioelectronics* 2003, 18, 1447-1453; A. K. Sharma et al., *Optics Communications* 2005, 245, 159-169; C. E. H. Berger et al., *Sensors and Actuators* B 2000, 63, 103-108; H. B. Lu et al., *Sensors and Actuators* B 2001, 74, 91-99; S. A. Zynio et al., *Sensors* 2002, 2, 62-70; J. R. Lakowicz, *Analytical Biochemistry* 2004, 324, 153-169 und N. Nath et al., *Anal. Chem.* 2002, 74, 504-509. Reference may also be made to a differential surface plasmon resonance measuring device and a corresponding measuring process according to EP 1617 203 A1 (T. Imato et al.).

A good overview of the basic principles of SPR sensors, types of implementation of SPR biosensors and applications of SPR biosensors is provided by various authors in the textbook "Surface Plasmon Resonance Based Sensors", *Springer Series on Chemical Sensors and Biosensors* (Ed. O. S. Wolfbeis), Volume 04 (Ed. J. Homola), Springer Verlag Berlin Heidelberg 2006.

An overview of developments and development objectives pursued in SPR biosensors is provided by Charles T. Campbell in an article entitled "Surface Plasmon Resonance (SPR) Biosensor Development" which can be downloaded from Internet on the following URL: www.cpac.washinqton.edu. This article also addresses differential SPR measurements in array format by means of what is known as SPR microscopy in which a 10×12 array is used with sixty measurement spots which are functionalized for binding sixty different biopolymers and sixty reference spots for subtracting background changes, in particular owing to non-specific binding and changes in the index of refraction of the buffer solutions.

The invention relates in particular to a technical solution in the field of analytical technology for physical, chemical and biochemical analysis. A particularly relevant application is, for example, determining the concentration of various substances in gaseous and liquid environments (cf. for example Class G01 N 21 of the International Patent Classification (IPC)), the carrying-out of biochemical analyses and immunological tests in medicine and in research, in biotechnology, for checking food quality, agricultural products and drinking water; this also includes determining the content of harmful substances (pesticides, insecticides, etc.), and also for the ecological monitoring of the environment. It may also involve the examination of adsorption processes, the highly sensitive measurement of temperature-dependent optical and electrical properties or examination of the change in these properties.

For the measurement of physical, biological, biochemical or chemical parameters, use is currently made above all of either direct or differential measurements. In the case of direct measurement, a measuring signal is read directly from an individual sensor. In the case of differential measurement, the signal is measured by an "active" sensor (also known as a measurement spot) and the signal, which is measured on an inactive sensor (also known as a reference spot), is subtracted from this measuring signal. Differential measurement allows the possible influence of a large number of disturbing factors and boundary conditions which it is impossible to check precisely, such as for example pressure, concentration of reagents, temperature and other parameters, to be prevented. The differential measuring assembly is well known and is used widely in technology and science. To give just a few examples: In physical sensors, differential measurements allow the influence of temperature to be minimized; in chemosensors and biosensors, the use of differential measurement allows not only the influence of temperature to be reduced but also non-specific effects on the surface of the sensor (for example adsorption of an interfering substance in affinity sensors, fluctuation of the oxygen partial pressure in enzymatic biosensors comprising a Clark electrode) to be compensated for. The use of differential measurements has been described in a large number of sources, in scientific publications and patent publications.

Nowadays, the sensitivity of many types of physical and chemical sensors is limited by fluctuations in temperature or fluctuations in the concentration of reagents or other physical and chemical parameters between the measurement spot and reference spot [A. Zybin et al., *Anal. Chem.*, 2005, 77, 2393-2399]. To reduce these effects, certain measuring apparatuses use highly precise temperature stabilization. Chemical sensors and biosensors use microfluidics which are relatively complex and not always reliable to reduce the fluctuations in temperature after addition of reagents, thus minimizing the difference in temperature between the reagents added and the surface of the sensor. In this case too, the fluctuations in temperature are not compensated for completely, as the interaction of the analyte with the measurement spot can take place as an exothermic or endothermic reaction. Additional difficulties which are not compensated for by highly precise temperature stabilization and microfluidics include fluctuations in the concentration of reagents in addition to the surface area or other physical parameters (for example pressure, reagent flow rate, etc.).

To improve compensation for disturbing factors, the measurement spot and the reference spot should be placed as close as possible alongside one another. However, this is not possible without limitation: although the measurement spot and the reference spot can be placed on a surface almost without a spacing, the measuring signals supplied by a measurement spot or reference spot are for most measuring methods integral signals of whole measurement surfaces. If there is a temperature gradient or a reagent gradient on the surface of the sensor (and inevitably there will be), signals from measurement spots and reference spots will be roughly the same as the signals at the centers of the spots. Therefore, not only the spacing between reference spots and measurement spots but also the size of the spots will characterize the minimum difference in temperature thereof. The size of the measurement spots and reference spots can be reduced only to a limited extent, as this typically leads to a reduction in the signal/noise ratio.

With regard to the nomenclature, it should be noted that the terms "measurement spot" and "sensor spot" are frequently—by way of distinction from the associated reference spot—used synonymously, although strictly speaking the reference spot can also be identified as a sensor spot, namely as a sensor spot of a type other than the measurement spot.

The invention is based on the object of preventing or at least greatly reducing the problems of the prior art without necessarily incurring high equipment costs.

SUMMARY OF THE INVENTION

To achieve this object, the invention proposes a sensor means comprising at least one arrangement of sensor spots which are arranged on or in a common substrate or held by a common substrate, wherein at least a first group of a plurality of sensor spots of the arrangement is configured as measurement spots which respond to at least one variable to be measured and based on which at least one measuring signal directly or indirectly representing the variable to be measured or a change in the variable to be measured can be provided by means of a measuring assembly, and at least a second group of a plurality of sensor spots of the arrangement is configured as reference spots which do not respond or respond only insignificantly to the variable to be measured and based on which at least one reference signal can be provided by means of the measuring assembly, the reference spots being configured relative to the associated measurement spots in such a way that the reference spots respond to at least one boundary condition variable to which the measurement spots also respond and which influences the at least one measuring signal such that the reference signal directly or indirectly represents the boundary condition variable or a change in the boundary condition variable, the sensor spots being arranged in a distributed manner such that both the reference spots and the measurement spots responding to the same variable to be measured are distributed over a common arrangement region such that such measurement spots are arranged between reference spots and reference spots are arranged between such measurement spots relative to at least one direction.

The solution according to the invention, which can aptly be described as "distributed referencing" (or sensors with distributed measurement spots and reference spots), is based on the following idea: instead of known measuring assemblies consisting of one (or more) measurement spot(s) and a reference spot, use is made of a plurality of small measurement spots and reference spots which are/become distributed on the measuring assembly. The total reference signal is measured from all or at least a plurality of selected reference spots. The measuring signal containing the measurement information itself is also measured from all or at least a plurality of selected measurement spots. The resulting output signal of the arrangement, for example for chemical or physical sensing, is obtained based on the measuring signal and the reference signal, for example by preferably program-controlled mathematical processing of these signals (typically by subtraction, i.e. calculating differences, or division, i.e. calculating ratios, with optional standardization).

The total surface area of all reference spots included in the measurement and all measurements spots included in the measurement can remain sufficiently large to prevent a negative effect on the signal-to-noise ratio (signal/noise ratio). The individual spots are however significantly smaller than conventionally used spots. Because the average spacing is defined by the size of individual spots and may thus—according to the invention—be very small, the invention allows very good compensation for fluctuations or changes in physical and chemical variables or boundary conditions to be obtained without losses in the signal-to-noise ratio, such as conceivable sensors which correspond to or take as their starting point the conventional approach and have overall a surface area which is as small as that of individual measurement spots and reference spots according to the invention but which yield a much worse signal-to-noise ratio or may, owing to an excessively low signal-to-noise ratio, even produce no evaluatable test results at all.

The invention proposes the use of distributed measurement spots and reference spots in physical, chemical and biological sensors based on locally resolved measurements, and corresponding sensors are provided. The "distributed referencing" allows, in particular, influences of temperature, fluctuations in temperature and non-uniform distributions of reagents in the measurements and also other disturbing variables and boundary conditions which are difficult to check to be compensated for; this improves the signal-to-noise ratio and signal-to-signal drift ratio.

A development of the sensor means according to the invention proposes that relative to the at least one direction for a plurality of measurement spots responding to the same variable to be measured and a plurality of reference spots or—preferably—for all measurement spots and/or all reference spots at least one of the following arrangement provisions is met:

i) relative to the at least one direction the measurement spots and the associated reference spots are arranged offset from one another in such a way that a respective measurement spot is arranged between two immediately adjacent reference spots;

ii) relative to the at least one direction the measurement spots and the associated reference spots are arranged offset from one another in such a way that a respective reference spot is arranged between two immediately adjacent measurement spots.

An expedient configuration provides for the sensor spots to be arranged in a distributed manner such that relative to at least one further direction measurement spots responding to the same variable to be measured are arranged between associated reference spots and reference spots are arranged between associated measurement spots responding to the same variable. Generally, however, it will be sufficient or even more expedient if the sensor spots are configured so as to be extended relative to a further direction and in this further direction measurement spots responding to the same variable and associated reference spots extend next to one another and if appropriate are not offset from one another.

A development proposes that the group of measurement spots comprises at least four, preferably at least eight, most preferably at least twelve, more preferably still at least twenty measurement spots which respond to the same variable and are distributed with the associated reference spots over the common arrangement region such that such measurement spots are arranged between reference spots and reference spots are arranged between such measurement spots relative to the at least one direction. It is further proposed that the group of reference spots comprises at least four, preferably at least eight, most preferably at least twelve, more preferably still at least twenty reference spots which are distributed with the measurement spots responding to the same variable to be measured over the common arrangement region such that such measurement spots are arranged between reference spots and reference spots are arranged between such measurement spots relative to the at least one direction.

Provision may advantageously be made for relative to the at least one direction for a plurality of measurement spots responding to the same variable to be measured—preferably at least four, most preferably at least eight, more preferably at least twelve, more preferably still at least twenty such measurement spots—and for a plurality of associated reference spots—preferably at least four, most preferably at least eight, more preferably at least twelve, more preferably still at least twenty reference spots—of measurement spots and reference spots which are immediately adjacent to one another to have a spacing of at most 3,000 µm, preferably a spacing of at most 300 µm, most preferably a spacing of at most 30 µm, more preferably a spacing of at most 10 µm or—more preferably still—to abut one another with an imperceptible or almost imperceptible spacing.

To allow measurement of different variables of a chemical, biological, biochemical or physical nature to be measured on the basis of a sensor means according to the invention, it is proposed that a plurality of first groups of sensor spots of the arrangement are each configured as measurement spots, the measurement spots of a group each responding to the or at least one same variable to be measured and the measurement spots of a plurality of different groups responding to various variables to be measured. In this connection, it is possible for a second group of sensor spots of the arrangement, which are configured as reference spots, to be jointly associated with the groups of measurement spots and for the measurement spots of the groups of measurement spots and the reference spots of the group of reference spots to be distributed over a common arrangement region. On the other hand, it is however preferable for each group of measurement spots to have associated with it its own second group of sensor spots of the arrangement, which are configured as reference spots and for, for each group of measurement spots and the associated group of reference spots its respective own common arrangement region to be provided, over which the measurement spots of the group of measurement spots and the reference spots of the associated group of reference spots are distributed and which is offset from the common arrangement region or regions of other groups of measurement and reference spots.

A development of the latter possible configuration proposes that the measurement spots of each group of measurement spots and the reference spots of the group associated therewith of reference spots are each distributed over the respective common arrangement region in such a way that relative to at least one direction the measurement spots are arranged between reference spots and reference spots are arranged between measurement spots. In this case, the measurement spots of each group of measurement spots and the reference spots of the group associated therewith of reference spots can each be arranged in the respective common arrangement region in accordance with the proposed developments of the invention discussed hereinbefore.

Advantageously, the sensor means may have at least four, preferably at least eight, most preferably at least twelve, more preferably still at least twenty different groups of measurement spots.

An embodiment which is particularly relevant in practice proposes that the sensor spots (measurement spots and reference spots) or a plurality of the sensor spots are arranged distributed on a preferably planar surface and preferably form at least one two-dimensional field of sensor spots that corresponds to a common arrangement region. In this case, the sensor spots arranged on the surface may be sheet-like in their configuration.

Another embodiment provides for the sensor spots (measurement spots and reference spots) or a plurality of the sensor spots to be arranged distributed in a volume and preferably to form at least one three-dimensional field of sensor spots that corresponds to a common arrangement region.

In particular for chemical, biological and biochemical measurement applications, a development of the sensor means according to the invention proposes that the measurement spots of the or each group are functionalized for at least one specific molecule or at least one molecule of a specific group of molecules to bind thereto and that the measuring signal represents the binding of at least one such molecule to a respective measurement spot or the amount of or a volume taken up by such molecules bound to a respective measurement spot as a variable to be measured. Furthermore, in particular for biological and biochemical measurement applications, a development of the sensor means according to the invention proposes that the measurement spots of the or each group are functionalized for at least one specific biological object or object fragment or at least one biological object or object fragment of a specific group of biological objects or object fragments to bind thereto and that the measuring signal represents the binding of at least one such object or object fragment to a respective measurement spot or the amount of or a volume taken up by such objects or object fragments bound to a respective measurement spot as a variable to be measured.

It is, for example, intended to detect DNA, antibodies, prions, bacteria, viruses and other objects and object fragments or molecules which are relevant in biosciences, biochemistry and biotechnology without having to produce a complete list. The invention is therefore not limited to specific applications and specific variables to be measured. Reference is also made in this connection to the specialist literature cited at the outset, which discloses corresponding functionalizations by way of example, and also to further examples which will be given hereinafter.

It is above all, but not exclusively, intended that a plasmon resonance, in particular surface plasmon resonance, can be excited in the substrate by preferably optical means and that the measuring signal and the reference signal are dependent on the excitation or non-excitation of a plasmon or surface plasmon resonance or on the interaction of the excited plasmon or surface plasmon with the environment in the region of a respective measurement spot or reference spot. Other measurement principles are however also possible.

The measuring assembly referred to may be a measuring assembly which is separate from the sensor means according to the invention. Preferably, however, the sensor means according to the invention comprises the measuring assembly for providing the measuring and reference signals.

The measuring and reference signals referred to are preferably provided by the measuring assembly based on optical and/or electrical interaction with the sensor spots (measurement spots and reference spots) or can be provided by the measuring assembly. A development proposes that the measuring assembly is configured to detect optical signals representing optical interaction between supplied electromagnetic radiation and the sensor spots and/or the environment thereof or a change in the optical interaction and to provide electrical signals or digital data representing the interaction or change in the interaction. For this purpose, the measuring assembly can comprise an image detection means, preferably a CCD or CMOS camera, or a detector field or detector array (for example a field or array of photodiodes) for detecting the optical signals.

A particularly preferred possible embodiment provides for the measuring assembly to be configured to provide individual measuring signals or reference signals for the measurement spots and the reference spots. It is however also possible for the measuring assembly to provide for all measurement spots included in a measurement and for all reference spots included in a measurement only a summary measuring signal or reference signal and optionally to detect also only summary (for example optical) original signals, i.e. it cannot carry out any measurement which is resolved relative to the individual spots. Measurement which is resolved or resolvable relative to the individual spots is however greatly preferred.

A development of the sensor means according to the invention proposes that the measuring assembly and/or an evaluation assembly associated therewith is configured to combine individual measuring signals and individual reference signals or sequence signals or sequence data obtained therefrom to form combination signals or combination sequence signals or combination sequence data, preferably to form summary or average measuring and reference signals or measuring and reference sequence signals or measuring and reference sequence data. In this connection, it is further proposed that the measuring assembly and/or an evaluation assembly associated therewith is configured to link the optionally standardized measuring and reference combination signals or measuring and reference combination sequence signals or measuring and reference combination sequence data or to subject them to at least one operation in order to obtain information about the variable to be measured or the change therein. It is in this connection intended above all that the measuring assembly and/or an evaluation assembly associated therewith is configured to calculate differences or ratios between the optionally standardized measuring and reference combination signals or measuring and reference combination sequence signals or measuring and reference combination sequence data in order to obtain information about the variable to be measured or the change therein.

The invention also provides, in particular, a sensor means which is configured as a surface plasmon resonance measuring means. Furthermore, the invention also provides, in particular, a sensor means which is configured as a chemosensor or biosensor means.

The invention is not however limited to specific measuring processes and measurement applications. For example, the sensor means may be configured as an ellipsometry measuring means, interferometry measuring means, fluorometry measuring means, absorbance measuring means, reflection measuring means, light scattering measuring means, acoustic measuring means, resonance frequency measuring means, cantilever measuring means, impedance measuring means or electrochemical measuring means, to name but a few examples. Further examples will be given hereinafter.

With regard to the boundary condition variable, it is intended inter alia that this variable is a variable from the group consisting of temperature, pressure, index of refraction, concentration, density and electrical potential. With regard to the various alternative configurations referred to hereinbefore of the sensor means, respective boundary conditions which influence the measurement and are possible for distributed referencing will be obvious to a person skilled in the art.

It is possible for the sensor means to measure a relatively large number of analytes at the same time by means of a field of sensors, in particular an array of sensors, without distributed referencing being carried out by means of the reference spot. For a measuring situation of this type, reference spots can on the one hand serve as measurement spots and at the same time—on the other hand—serve to a lesser or greater extent as reference spots for other analytes or other variables to be measured. It is generally proposed in this regard that sensor spots which serve as reference spots and are optionally functionalized for this purpose serve as measurement spots relative to at least one other variable to be measured, in particular are functionalized for this purpose. Furthermore, it is also intended in this connection that sensor spots which serve as measurement spots and in particular are functionalized for this purpose serve as reference spots, and optionally are functionalized for this purpose, relative to at least one other variable to be measured.

In the case of measurement without distributed referencing, the signals can be processed using methods which are generally relatively complex, for example by means of multiparametric statistics (for example principal component analysis) by means of neural networks or other artificial intelligence algorithms and also other methods which are known per se for measuring situations of this type. The evaluation assembly of the measuring assembly according to the invention can be configured or programmed for this purpose.

The invention further generally provides a device for sensor or transducer applications, in particular for chemosensor and biosensor applications, comprising or consisting of a sensor spot or transducer spot arrangement having at least two spots of type A, referred to hereinafter as "spots A", and at least two spots of type B, referred to hereinafter as "spots B", A denoting any desired specific configuration, in particular coating and construction, of the spots A and B denoting any desired specific configuration, in particular coating and construction, of the spots B. The invention provides for the spots A and B to be distributed on a surface and/or in a volume and for electrical and/or optical signals of the spots A and the spots B to be able to be measured. The device according to the invention can comprise an apparatus for measuring the electrical and/or optical signals.

A development of the device proposes that the spots A comprise a plurality of groups of spots of a different subtype $A_x$, wherein $A_x$ denotes any desired specific configuration, in particular coating and construction, of the spots of the respective subtype $A_x$, referred to hereinafter as spots $A_x$.

The spots of type A or of a subtype $A_x$ can serve as measurement spots and the spots of type B can serve as reference spots.

The device according to the invention can comprise a sensor means according to the invention as defined hereinbefore and described with regard to developments or be formed by such a sensor means. In this case, the reference spots may be identified as spots of type B and the measurement spots may be identified as spots of type A or the measurement spots of a specific group of measurement spots may be identified as spots of subtype $A_x$.

The device according to the invention for sensor or transducer applications will also be referred to hereinafter as a "sensor device" or simply as a "device" for short.

The invention also provides, in particular, a sensor device for use in chemosensor and biosensor applications, comprising at least two spots with a coating and construction of type A (wherein A denotes any desired coating and construction, referred to hereinafter as "spots A") and at least two spots with a coating and construction of type B (wherein B denotes any desired coating and construction, referred to hereinafter as "spots B"), the spots A and B being distributed on the surface and/or in a volume. The device can comprise an apparatus or an assembly for measuring electrical and/or optical signals of individual types of spots (type A or type B) or be provided to interact with an apparatus of this type or an assembly of this type. The spots A are preferably measurement spots in the above-described sense and the spots B are preferably reference or calibration spots in the above-described sense. It is also conceivable for the device to have a plurality of groups of spots of type A, each group comprising at least two spots with a coating and construction of a subtype $A_x$, (wherein $A_x$ denotes any desired coating and construction).

Preferably, the sensor device has at least eight spots with a coating and construction of type A and at least eight spots with a coating and construction of type B.

The invention further provides an arrangement consisting of $\eta$ sensor devices of this type, wherein $\eta$ is between 2 and 10,000,000, in particular between 4 and 400. Spots A in the individual devices can have the same or different coating and/or construction ($A_1$, $A_2$, ... $A_n$), wherein the spots B preferably have the same coating and the same construction in all devices.

The spacing between immediately adjacent spots (i.e. spots located next to one another) may expediently be between 0 und 3,000 µm, in particular between 0 und 10 µm, a spacing of 0 meaning that a respective spot A and a respective spot B abut one another.

Preferably, the spots A and B are located on a flat surface and are in this case preferably sheet-like in their configuration. Alternatively, provision may be made for the spots A and B to be distributed not on a surface but rather in a volume.

It is intended above all—but not exclusively—that the signals to be measured of the individual spots or—likewise in principle possible—the signals to be measured resulting from the signal contributions of a plurality of spots are optical signals. The optical signals of individual spots can, for example, be measured with a device for the recording of optical images (preferably a CCD camera or CMOS camera).

The device according to the invention can additionally comprise a measuring assembly for generating and measuring surface plasmon resonance or be configured to interact with an assembly of this type.

Furthermore, the device according to the invention can additionally comprise a measuring assembly for ellipsometric measurements or be configured to interact with an assembly of this type.

Furthermore, the device according to the invention can additionally comprise a measuring assembly for fluorometric measurements or be configured to interact with an assembly of this type.

Furthermore, the device according to the invention can additionally comprise a measuring assembly for measuring optical absorbance, localized plasmon resonance, reflection or light scattering or be configured to interact with an assembly of this type.

Furthermore, the device according to the invention can additionally comprise a measuring assembly for generating and measuring surface acoustic waves or resonance frequencies of oscillating crystals or microcantilevers or be configured to interact with an assembly of this type.

Furthermore, the device according to the invention can additionally comprise a measuring assembly for impedance measurements and/or electrochemical measurements or be configured to interact with an assembly of this type.

Advantageously, the device according to the invention can additionally comprise a digital or analog signal processor or be configured to interact with a processor of this type. The signal processor can be configured or programmed to evaluate the data of the spots A and the spots B. It is intended especially—but not exclusively—that the processor computes the signal sums for the individual types of spot $A_1$, $A_2$, ..., $A_n$, B and calculates the values ($\alpha_1 A_1$-B), ($\alpha_2 A_2$-B), ..., ($\alpha_n A_n$-B) or $\alpha_1 A_1/B$, $\alpha_2 A_2/B$, ..., $\alpha_n A_n/B$. The values $\alpha_1$, $\alpha_2$, ... $\alpha_n$ are preferably constant. If the signal values are independent of the spot surface area, the $\alpha$ values may assume the value 1. Otherwise, the $\alpha$ values will generally denote a surface area ratio: $\alpha_i$=(spot surface area B/spot surface area A). It is entirely possible for the $\alpha$ values to be dependent on the materials and the construction of the spots A and B. If only spots A of one type are present, it may also be possible to calculate within a measurement only one signal sum for spots A and one signal sum for spots B, from which ($\alpha$A−B) or $\alpha$A/B may then typically be calculated.

An application of the device according to the invention for determining the index of refraction of a liquid, gaseous or solid medium is, for example, envisaged.

Furthermore, an application of the device according to the invention for detecting the binding of molecules (in particular for example DNA, RNA, proteins, sugars, polysaccharides, antibodies, hormones, lipids, signal transmission mediators, pharmaceutical substances, metabolites, toxins), molecular complexes, cell organelles, cells, viruses, bacteriophages, prions to the corresponding receptors is, for example, envisaged.

The provision of the device according to the invention or use of the device according to the invention as a biosensor and/or chemical sensor is envisaged. The provision of the device according to the invention or use of the device according to the invention as a DNA or RNA probe is, in particular, also envisaged.

Insofar as the scope of the invention or the application thereof includes measurement data collection which is accessible to image detection or is based on a type of image detection, preferably digital filtration of detected images for the detection and recognition of artificial or natural objects, in particular for example in a size range of up to 100 µm, can advantageously be provided.

According to an important aspect, the invention provides a multi-sensor array for analytical, bioanalytical or physical examinations, or the device according to the invention can be used as a multi-sensor array for examinations of this type.

The above-defined sensor means of the invention, which has been described with regard to preferred developments, can comprise a device according to the invention for sensor or transducer applications or a sensor device or device as described hereinbefore or be formed by a device of this type.

The invention further provides a measuring process, carried out using a sensor means according to the invention or a device according to the invention.

The "distributed referencing" according to the invention can be used independently of conventional complex microfluidics and highly precise temperature stabilization, the measurement construction being simplified accordingly. The "distributed referencing" can therefore be used as an alternative to previous solutions, or else be used in conjunction with the microfluidics or highly precise temperature stabilization, to achieve better compensation.

The physical and chemical sensors with distributed referencing can be constructed as individual differential sensors or as sensor arrays. In the latter case, use is made of a plurality of different groups of sensor spots which are distributed in any desired manner (but preferably relatively uniformly) (with the same type of sensor in each group) and of reference spots which are distributed in any desired manner (but preferably relatively uniformly).

The application of the proposal of the invention in conjunction with surface plasmon resonance sensors and measurements (SPR) is especially—but not exclusively—envisaged. The proposal of the invention can however advantageously also be applied in conjunction with completely different types of sensors and measuring processes.

Thus, for example, optical chemosensors and biosensors based on ellipsometry or interferometry have very similar structures to SPR sensors and have to contend with the same or similar artifacts. Local fluctuations and gradients of the temperature and other parameters are also critical in other methods, for example in fluorescent biosensors and chemosensors, in particular DNA arrays.

As was also proposed for SPR sensors, according to the invention DNA arrays can, for example, be configured with distributed reference spots. It is proposed to provide a plurality, in particular a large number of identical reference spots and measurement spots.

In principle, spots of the same type can be arranged in any desired manner relative to one another; the spacing between the reference spots, on the one hand, and the measurement spots, on the other hand, should merely be minimized.

The data can be evaluated by calculating the difference between the mean values of the signals of the reference spots and measurement spots, as will be described as an example hereinafter in greater detail, in principle relative to SPR sensors.

Distributed reference and sensor spots according to the invention allow the signal-to-noise ratio to be improved even in measuring processes using DNA arrays with fluorescent detection, which are based on fluorescent intercalators (for example Hoechst 33258, Hoechst 33342, ethidium bromide, TOTO, PicoGreen or any other dye which is conventional in the field) or reporter sequences with fluorescent labels. In contrast to a proposal for referencing of fluorescence intensity signals according to DE 198 29 657 A1 (I. Klimant), which is based on fluorescence signals of two or more luminophores, the use according to the invention of distributed reference and sensor spots allows the measurement to be based on fluorescent signals of only one luminophore.

The "distributed referencing" according to the invention can furthermore be used in mechanical-acoustic transducers for chemosensors and biosensors, especially if the transducers are used as an array (for example transducers based on surface acoustic wave (SAW) devices or micro cantilevers).

The "distributed referencing" according to the invention can furthermore be used in electrochemical chemosensors and biosensors, for example in chemical and biological sensors based on impedance measurements, lateral conductivity measurements of conductive polymers or electrochemical measurements of the rate of enzymatic reactions.

The "distributed referencing" according to the invention can also be used in physical sensors, for example in photodetectors.

In addition to the range of SPR applications, various other detection methods (for example ellipsometry, interferometry, fluorescence, optical absorbance, light scattering, localized plasmon resonance), mechanical-acoustic measuring methods (for example SAW, microcantilevers), electrical measuring methods (for example conductivity changes of conductive polymers) and electrochemical measuring methods (for example chronoamperometry, impedometry, voltammetry, potentiometry, etc.) are therefore also possible for applying the proposal of the invention, corresponding transducers or sensor devices being provided and used. In chemosensors and biosensors, a "transducer" is used to convert "chemical" values or variables (for example the quantity of molecules which are bound to the receptor layer on a sensor surface or the rate of the enzymatic reaction in an enzyme layer on the sensor surface) into physical values or variables (for example light intensity, wavelength, oscillation frequency, strength of electric current or voltage or electrical potential).

BRIEF DESCRIPTION OF THE DRAWINGS

The invention will be described hereinafter in greater detail with reference to the examples and diagrams shown in the figures and the examples given below. In the drawings.

DETAILED DESCRIPTION OF THE INVENTION

Figure 1:
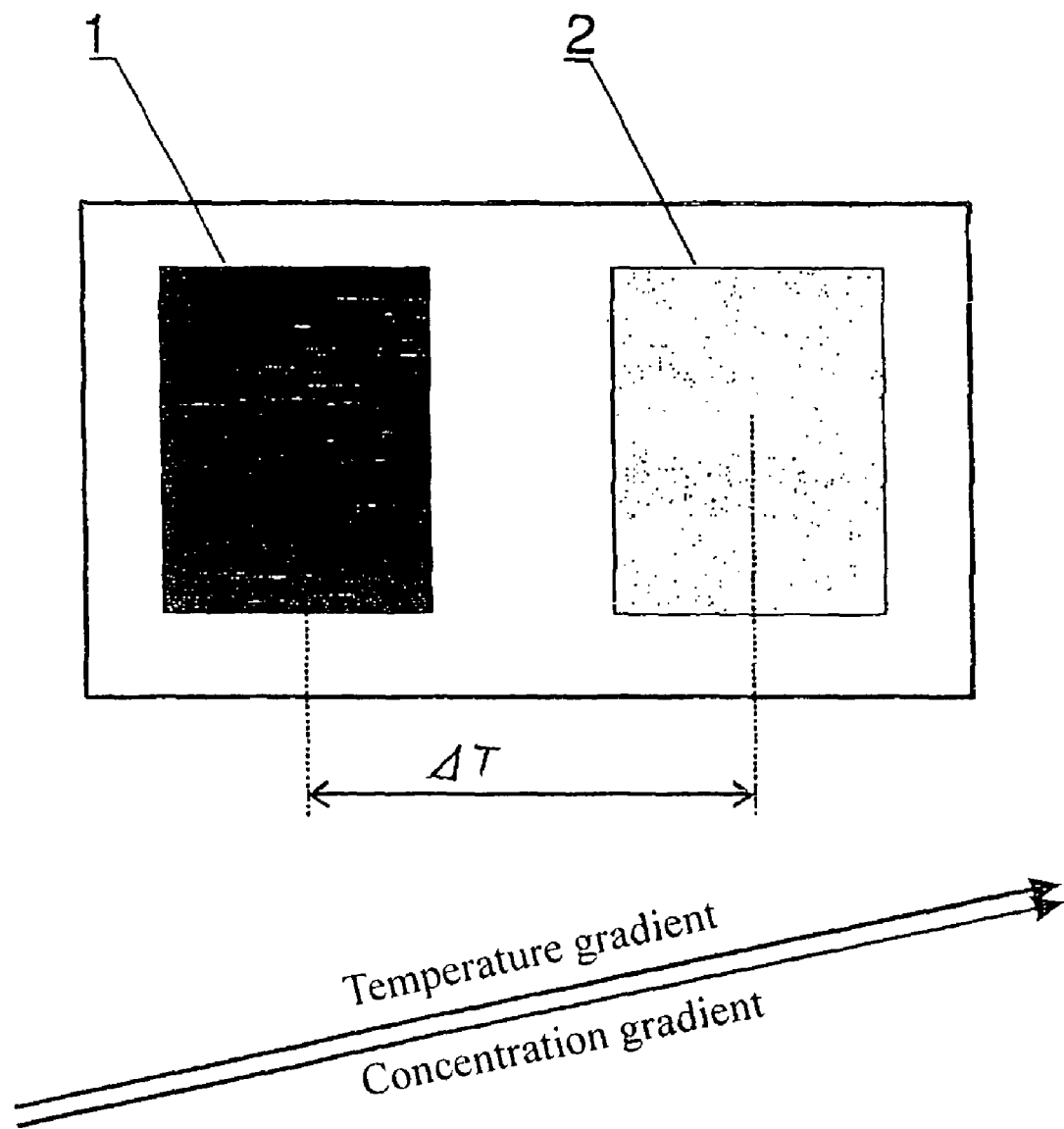
FIG. 1 illustrates a difference in temperature and/or concentration of reagents between a measurement spot (black) and a reference spot (light grey) for conventional macroscopic sensors.

FIG. 1 shows a conventional arrangement consisting of a measurement spot 1 and a reference spot 2. An inflow of a reagent solution, for example, produces during the measurement a temperature gradient (represented by an arrow), so there is a difference in temperature $\Delta T$ between an average temperature of the measurement spot 1 and an average temperature of the measurement spot 2. If, for example, a chemical or biological variable is measured in a surface plasmon resonance measurement by means of the measurement spot 1 and the variable is corrected by means of a reference measurement based on the reference spot 2, the correction is, in accordance with the difference in temperature $\Delta T$, defective or incomplete. The smaller the difference in temperature $\Delta T$ between the measurement spot and the reference spot, the better the correction may be. As the average effective spacing between the measurement spots and reference spots depends on the average size of the spots, the conventional approach does not allow the spacing between spots to be reduced as desired, so considerable differences in temperature $\Delta T$ remain unless expensive equipment is used to ensure that the temperature gradient is minimized. The same applies to other parameters influencing the measurement, for example the gradient of a concentration of a reagent solution (represented by an arrow) or the like.

It should be noted that the situation, described with reference to FIG. 1, of the conventional approach is in no way changed even if the size of the interval shown in FIG. 1 between the measurement spot 1 and the reference spot 2 is reduced and the measurement spot and the reference spot directly abut one another. Also critical is the spacing between the spots relative to the centers of the spots, as at least on rough examination the measuring signals of the measurement spot and of the reference spot generally correspond over the respective surface of the spot, despite the temperature gradient or other gradients, to a respective signal which would be obtained for a spot which is subject over its entire surface to a temperature or other boundary conditions corresponding to the temperature or the boundary conditions at the center of the spot. This is true in any case of measuring methods which yield integral signals of whole measurement surfaces.

Figure 2:
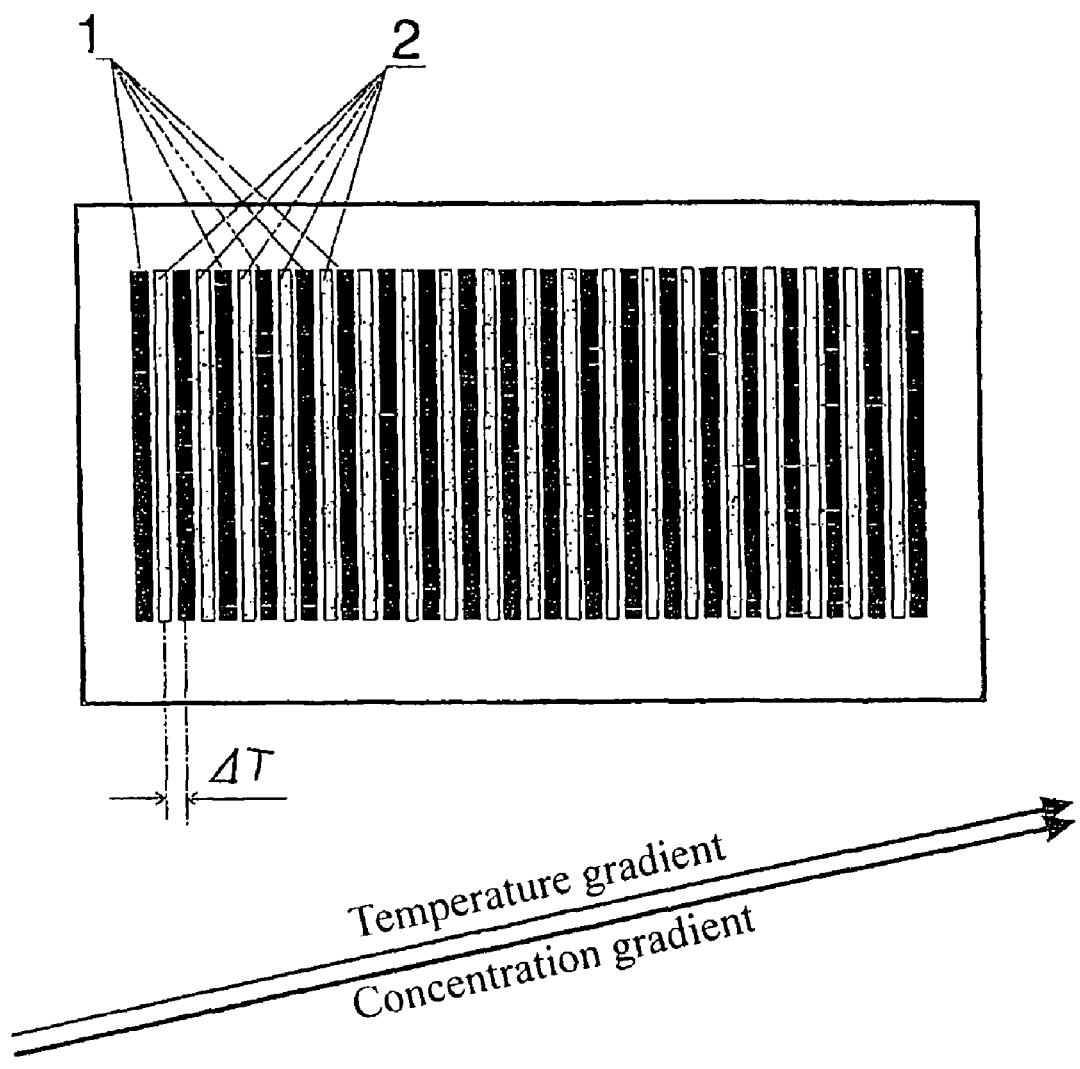
FIG. 2 illustrates a difference in temperature and/or concentration of reagents between a measurement spot (black) and a reference spot (light grey) for a sensor according to the invention with distributed sensor and reference spots.

FIG. 2 shows, on the other hand, an example of a field according to the invention of distributed measurement spots 1 and reference spots 2. The measurement and reference spots are distributed along a direction in such a way that—apart from the edge spots—a respective measurement spot is arranged between two immediately adjacent reference spots and a respective reference spot is arranged between two immediately adjacent measurement spots and the spacing between adjacent measurement and reference spots is smaller than the extension of the measurement and reference spots in this direction. A difference in temperature $\Delta T$ which occurs between adjacent measurement spots and reference spots for a given temperature gradient is thus substantially smaller than that which would be obtained for the same temperature gradient for conventional measurement and reference spots according to FIG. 1. The same applies to other gradients such as gradients of concentrations, etc.

As a plurality or large number of measurement and reference spots are provided, an adequate or even very good signal-to-noise ratio, which depending on the effective total surface area is even significantly better than in the conventional solution according to FIG. 1, can overall be achieved despite the low extension of the spot in the distribution direction. In particular, even a significantly improved signal-to-signal drift ratio can be achieved and overall a significantly improved measuring sensitivity can be attained, as artifacts and drifts which limit the measuring sensitivity can be effectively compensated for owing to varying and differing measurement boundary conditions between the measurement spots and reference spots. On graphic examination, it is possible to imagine the provision for each measurement spot of at least one respective closely adjacent reference spot which is subject to almost the same measurement boundary conditions and thus effectively allows compensation of the measurement. For this purpose, it is possible to carry out signal processing which takes into account the signals of all or a plurality or a large number of selected measurement spots and reference spots. This leads to a reduction in signal contributions owing to fluctuations in temperature and other fluctuations, for example in pressure, a reagent fluctuation or other parameters, down to a level at which the resulting signal fluctuations are lower than those between two adjacent miniaturized measurement spots and reference spots. As the total surface area of the spots remains macroscopic, the shot noise and other noise sources, which relative to the surface area of an individual spot would be relevant or even limiting owing to the miniaturization thereof, are eliminated. Furthermore, the low effective spacing between the measurement spots and reference spots ensures rapid diffusion of heat and prevents or reduces local temperature gradients resulting for example from analyte-receptor interactions, for example exothermic or endothermic effects owing to binding of the analyte to a respective receptor.

Figure 3:
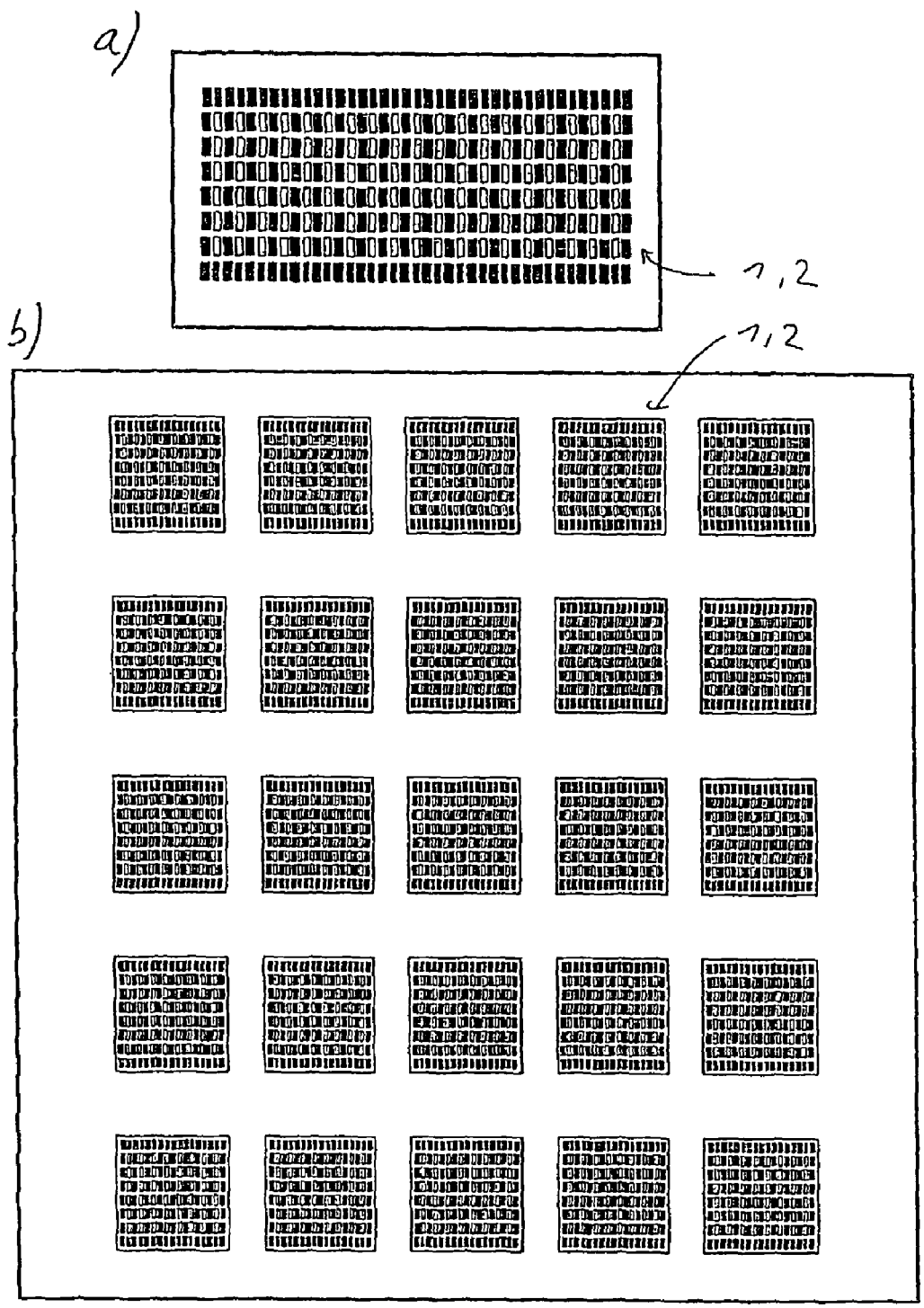
FIG. 3 shows in Partial FIG. 3a a single sensor with distributed measurement spots and reference spots and in Partial FIG. 3b a sensor array with distributed measurement spots and reference spots.

A sensor according to the invention can have an individual field of sensors with distributed sensor and reference spots, as illustrated in FIG. 3a, or be configured as a sensor array and have a plurality of fields with distributed sensor and reference spots, as illustrated in FIG. 3b. For each field, the measurement spots are functionalized for measuring the same chemical, biological or other variable. If, as in FIG. 3b, a plurality of fields of measurement spots and reference spots are provided, each field can be provided for measuring a different chemical, biological, physical or other variable, if the measurement spots are functionalized for this purpose. A plurality of variables can thus be measured simultaneously.

Figure 4A:
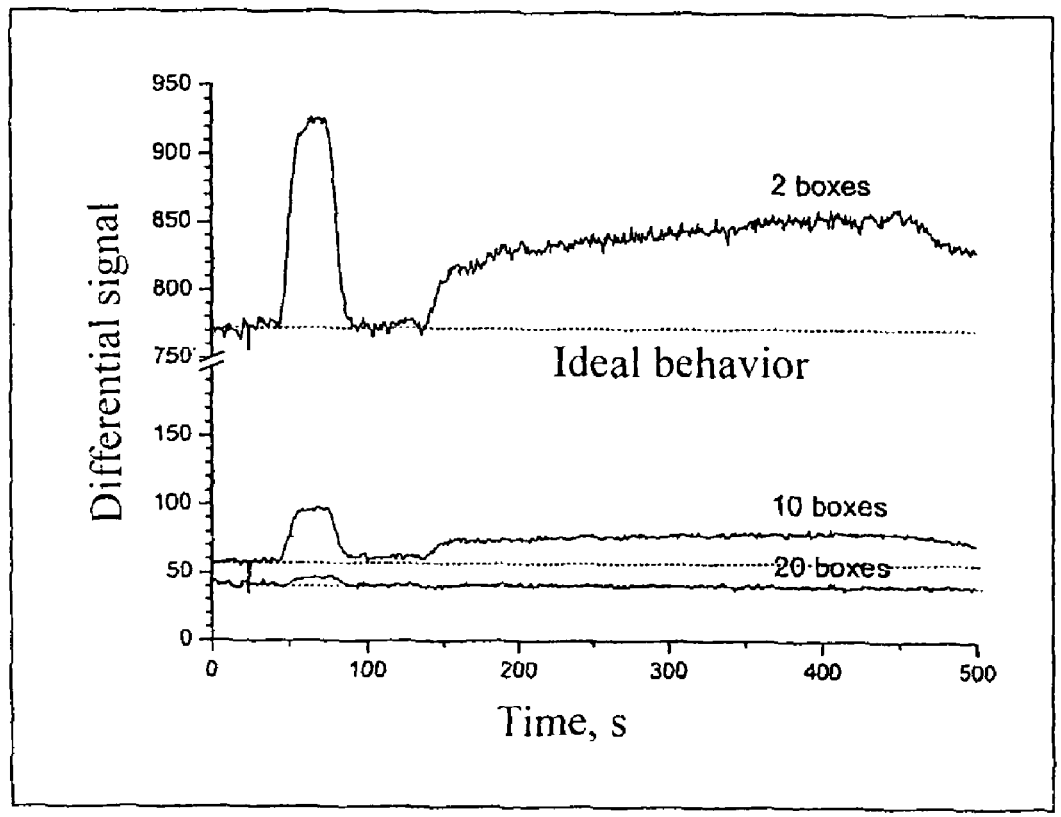
FIG. 4 shows in Partial FIG. 4a a diagram which demonstrates the effectiveness of the distributed referencing based on a measured signal difference between identical spots, based on measurements taken from spot arrangements according to Partial FIG. 4b.

FIG. 4a shows a test result for the signal difference between identical spots in an SPR measurement, of which one or a group is used as reference spots and one or a group is used as measurement spots, after the addition of hot electrolyte to a flow cell of the SPR measuring assembly. For the purposes of comparison, measurements were carried out on the following arrangements of reference spots and measurement spots illustrated schematically in FIG. 4b: one reference spot and one measurement spot ("2 boxes"), linearly distributed structures consisting of five reference spots and five measurement spots ("10 boxes"), linearly distributed structures consisting of ten reference spots and ten measurement spots ("20 boxes"). The coating of the reference spots (denoted in FIG. 4b by "R") and measurement spots (denoted in FIG. 4b by "S") and the total surfaces are identical, so ideally the signal difference should disappear, i.e. be equal to zero, owing to complete compensation for the temperature gradient which occurs. The results show that the signal difference between distributed measurement spots and reference spots is much closer to the ideal behavior (dotted lines) than in the conventional solution with one reference spot and one measurement spots.

Figure 5:
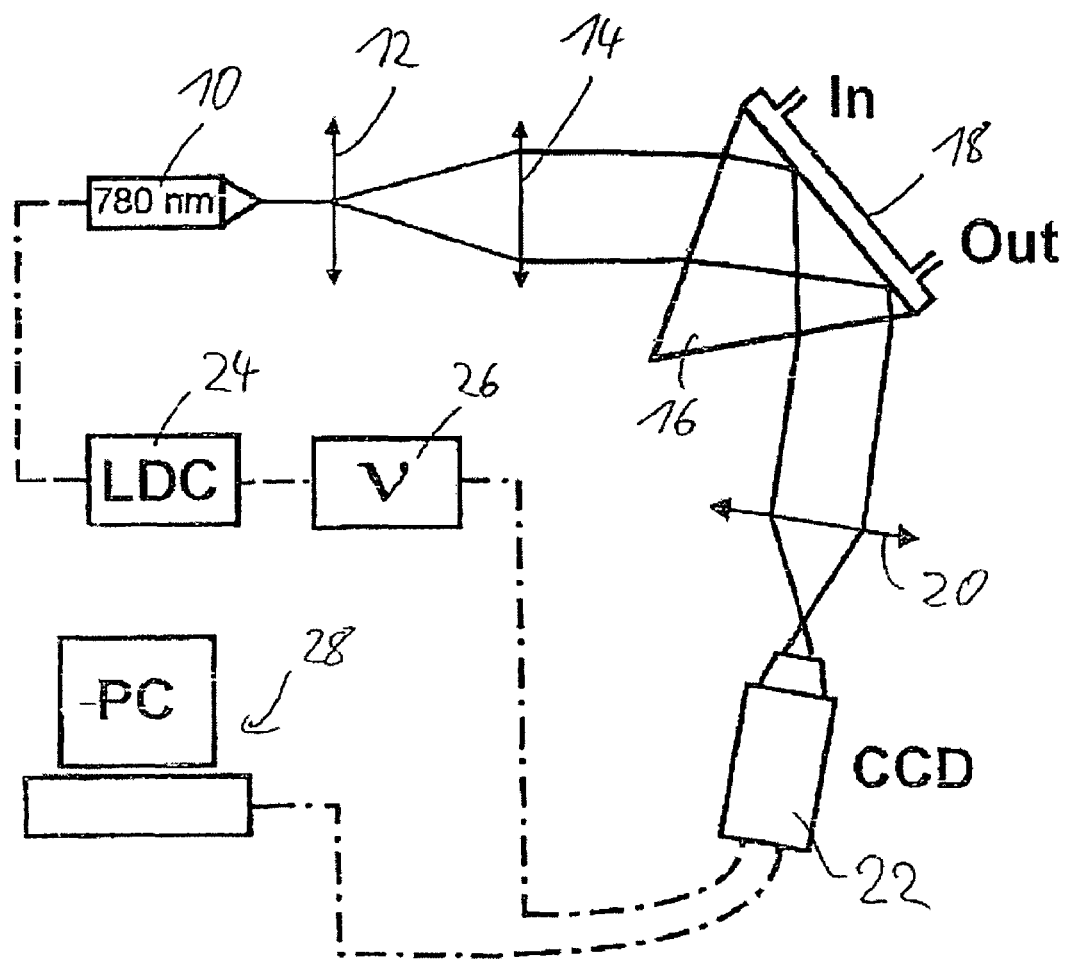
FIG. 5 shows an exemplary SPR measuring construction which can be used within measurements on the basis of the distributed referencing according to the invention.

A typical measuring construction for an SPR measurement is shown in FIG. 5. A laser beam of a laser diode 10 (for example having a wavelength of 784 nm) is widened by two lenses 12, 14 to a diameter of approximately 3 cm. A prism 16, which is used for generating an SPR resonance and into which the widened laser beam is coupled, has for example an entry area of 2×1 cm$^2$. A flow cell 18, made for example of Plexiglas, is attached to the back, which is coated with a suitable metal layer, in the present case a gold layer, of the prism. For measurements according to the invention, a field of spots according to the invention, with distributed measurement spots and reference spots, is configured on the metal layer, for example as shown in FIG. 2, FIG. 3a or FIG. 3b, or as shown in FIG. 4b, center or bottom. Light which is reflected by the gold surface is detected in a locally resolved manner by a CCD camera 22 with the aid of optics 20. For achieving a type of lock-in metrology, the CCD camera 22 and a laser driver circuit 24 are synchronized by a square wave generator 26 at a frequency of 1 kHz. A CCD camera may, for example, be a modified MV14-285 camera with 36,000 electrons per pixel, with a CCD chip size of 1,024×1,360 pixels. The charge integrated in the pixels is then converted with 14-bit resolution into a digital signal and transferred to a computer (PC) 28 by way of a frame grabber card for further evaluation. Locally resolved detection of the measuring signals or reference signals is thus possible for each individual measurement spot and reference spot of the distributed measurement and reference spots.

The measurement and data analysis in a differential SPR measurement can be carried out based on a typical SPR measuring situation on application of the proposal of the invention and, for example, using the arrangement according to FIG. 5, for example as follows:

1. The measurement spots and reference spots are calibrated. For this purpose, the water in the flow cell is exchanged for a calibration solution (for example 0.1% NaCl), and the change in the SPR signal is measured on all spots. Based on this solution, the signals of all spots are converted into absolute units (refractive index units—RIUs). The calibration permits allowance to be made for local non-uniformities in the surface of the sensor, for example non-uniform thickness of the gold layer.

2. Analyte is added and the signals of all spots or of selected spots are measured.

3a. The (arithmetic) mean value of the signals of all or of selected measurement spots (spots of type A) is computed (denoted hereinafter by <A>).

3b. The (arithmetic) mean value of the signals of all or of selected reference spots (spots of type B) is computed (denoted hereinafter by <B>).

4. The difference <A>-<B> is calculated.

The same applies to other SPR measuring situations. Similarly, the signals can be calculated, if the distributed referencing according to the invention is used, also in other detection methods, for example in ellipsometry, interferometry, local plasmon resonance on monolayers of nanoparticles, micro cantilevers, SAW (surface acoustic wave) apparatuses, fluorescence intensity, etc.

If use is made of signals which are dependent on the surface area of the sensor (for example measuring the electrical capacitance or electric current), the signal of each spot can expediently be standardized to the surface area of the corresponding spot or the mean value of the signals can be standardized to the total surface area of the corresponding spots.

In some cases, the measured signal is exponentially dependent on the concentration of the analyte (for example if use is made of optical sensors, the behavior of which is described by Lambert-Beer's Law). In this case, the signals can expediently be analyzed by calculating the ratio <A>/<B>. If there are only small signal changes, the above-mentioned calculation method <A>-<B> can be applied in this case, too.

In data analysis methods for sensors based on the fluorescence decay time, the dependency of the decay time on the concentration of the analyte can also be used.

Example 1

An application of distributed referencing in surface plasmon resonance biosensors will be demonstrated. An SPR microscope with a CCD camera is used for the measurements. The microscope may be embodied differently, as shown for example in FIG. 5, or be embodied using double-wavelength technology [*Anal. Chem.* 2005, 77, 2393-2399]. The resonance layer used is a vapor-deposited, 60 nm-thick gold layer with a 5 nm-thick chromium adhesion layer. The reference spots were coated with the thiol derivative having the structure HS—$(CH_2)_{11}$—(O—$CH_2$—$CH_2)_4$—OH. The reference spots are 100×100 μm in size and are located on a gold surface, distributed like "white squares on a chess board". The remaining gold surface (which is distributed like "black" 100×100 μm chessboard squares) was coated with 1,15-mercaptohexadecanoic acid. The locally resolved coating was carried out using one of the previously known technologies, for example by means of microstamp technology [H. O. Jacobs et al., WO 02/03142 A2], using a commercial nanoplotter or as electrically addressable immobilization [V. M. Mirsky et al., U.S. Pat. No. 6,458,600 B1]. The latter technology requires corresponding structuring of the gold layer, which can be achieved using photolithographic processes. Subsequently, a receptor layer (for example anti-HSA antibodies) was immobilized on COOH groups of the immobilized 1,15-mercaptohexadecanoic acid. Immobilization technology using water-soluble carbodiimide (EDC) has been described in detail in the specialist literature [V. M. Mirsky et al., *Biosensors & Bioelectronics*, 1997, 12, 977-989], [N. Wrobel et al., *Colloids and Surfaces B: Biointerfaces*, 2003, 32, 157-162]. Signal detection takes place as in [*Anal. Chem.*, 2005, 77, 2393-2399], but with a CCD camera and corresponding optics instead of a photodiode. The comparison of the signal-to-noise ratio and also of the signal drift measured with and without distributed referencing reveals an approx. 10 to 50-fold improvement for distributed referencing over conventional referencing.

Example 2

Figure 6:
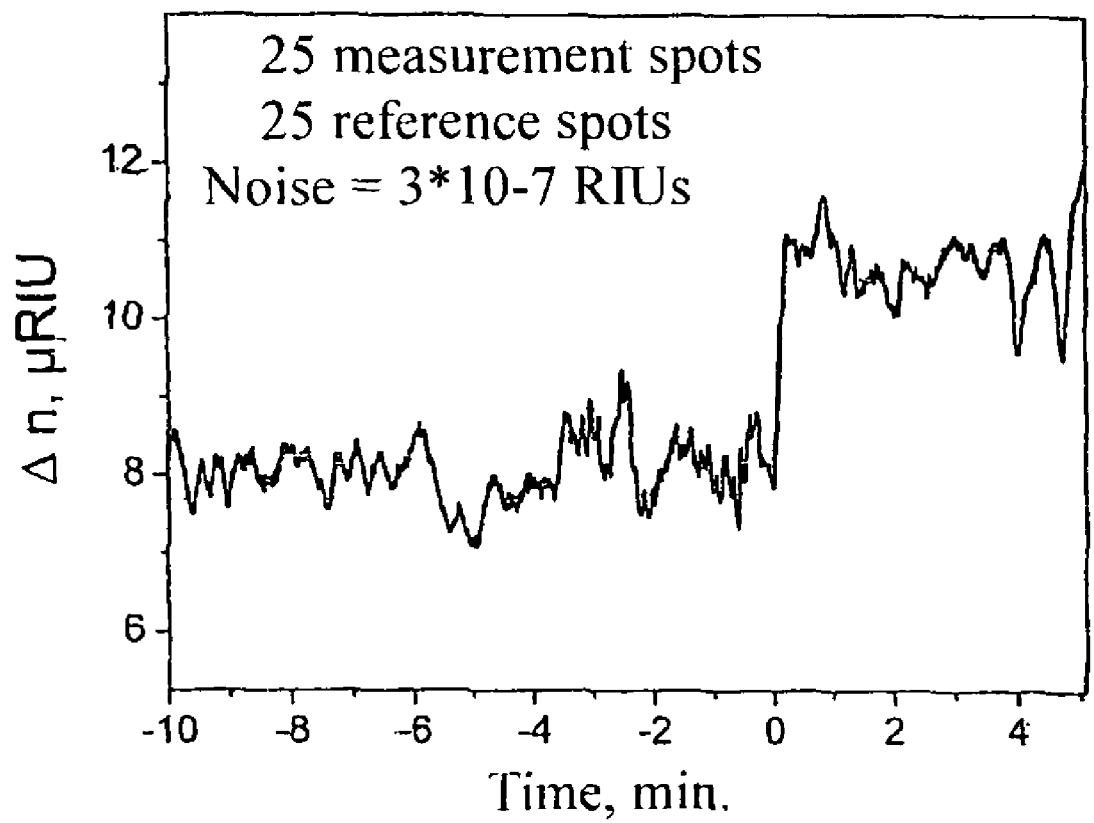
FIG. 6 shows a diagram which demonstrates the effectiveness of the distributed referencing in a biosensor application.

An example of the detection of small molecules using the distributed referencing procedure or method is shown in FIG. 6. The following spot layout was used: strip-like measurement spots and reference spots having a respective width of 200 μm; in total 50 strips, namely 25 measurement spots or measurement strips and 25 reference spots or reference strips. The strip length is approx. 1.2 mm and there is almost no spacing between adjacent measurement strips and reference strips. As shown in FIG. 2, the measurement and reference strips are arranged alternately.

The measurement strips are coated with a monomolecular layer of streptavidin. At moment zero 1 μmol/L of biotin was injected into the flow cell. There resulted immediately an abrupt rise in the curve as a result of the fact that the biotin molecules rested against the streptavidin layer. The noise during the measurement was approximately $3 \times 10^{-7}$ the refractive index units RIUs. The signal-to-noise ratio for the detection of biotin was approximately 10.

The signal-to-noise ratio which may roughly be expected for a conventional measurement without distributed referencing is markedly dependent on the SPR configuration used. For the simplest configuration, based on measurement with the distributed referencing according to FIG. 6 (without special thermostatting, without double wavelength technology, etc.), it would be almost impossible, for an identical coating, to carry out the detection of biotin, as a signal-to-noise ratio of <1 would be expected.

Proposed is a sensor means comprising at least one arrangement of sensor spots which are arranged on or in a common substrate or held by a common substrate, wherein at least a first group of a plurality of sensor spots of the arrangement is configured as measurement spots which respond to at least one variable to be measured and based on which at least one measuring signal directly or indirectly representing the variable to be measured or a change in the variable to be measured can be provided by means of a measuring assembly, and at least a second group of a plurality of sensor spots of the arrangement is configured as reference spots which do not respond or respond only insignificantly to the variable to be measured and based on which at least one reference signal can be provided by means of the measuring assembly, the reference spots being configured relative to the associated measurement spots in such a way that the reference spots respond to at least one boundary condition variable to which the measurement spots also respond and which influences the at least one measuring signal such that the reference signal directly or indirectly represents the boundary condition variable or a change in the boundary condition variable. According to the invention, provision is made for the sensor spots to be arranged in a distributed manner such that both the reference spots and the measurement spots responding to the same variable to be measured are distributed over a common arrangement region such that such measurement spots are arranged between reference spots and reference spots are arranged between such measurement spots relative to at least one direction.

The invention claimed is:

1. A plasmon resonance sensor means comprising at least one arrangement of sensor spots which are arranged on or in a common substrate or held by a common substrate, wherein at least a first group of a plurality of sensor spots of the arrangement is configured as measurement spots which respond to at least one variable to be measured and based on which at least one measuring signal directly or indirectly representing the variable to be measured or a change in the variable to be measured is provideable by means of a measuring assembly, and at least a second group of a plurality of sensor spots of the arrangement, which are associated with the measurement spots, is configured as reference spots which do not respond or respond only insignificantly to the variable to be measured and based on which at least one reference signal is provideable by means of the measuring assembly, wherein a plasmon resonance is excitable in the substrate and the measuring signal and the reference signal are dependent on the excitation or non-excitation of a plasmon resonance or on the interaction of the excited plasmon with the environment in the region of a respective measurement spot or reference spot, the reference spots being configured relative to the associated measurement spots in such a way that the reference spots respond to at least one boundary condition variable to which the measurement spots also respond and which influences the at least one measuring signal such that the reference signal directly or indirectly represents the boundary condition variable or a change in the boundary condition variable, the sensor spots being arranged in a distributed manner such that both the reference spots and the measurement spots responding to the same variable to be measured are distributed over a common arrangement region such that such measurement spots are arranged between reference spots and reference spots are arranged between such measurement spots relative to at least one direction, wherein relative to the at least one direction for a plurality of measurement spots responding to the same variable to be measured and a plurality of reference spots or preferably for at least one of all measurement spots and all reference spots, at least one of the following arrangement provisions is met:

i) relative to the at least one direction the measurement spots and the associated reference spots are arranged offset from one another in such a way that a respective measurement spot is arranged between two immediately adjacent reference spots;

ii) relative to the at least one direction the measurement spots and the associated reference spots are arranged offset from one another in such a way that a respective reference spot is arranged between two immediately adjacent measurement spots, wherein the group of measurement spots comprises at least four measurement spots which respond to the same variable and are distributed with the associated reference spots over the common arrangement region in accordance with the arrangement provision such that such measurement spots are arranged between reference spots and reference spots are arranged between such measurement spots relative to the at least one direction, wherein at least one of the measuring assembly and an evaluation assembly associated therewith is configured to combine individual measuring signals of the measurement spots responding to the same variable to be measured and individual reference signals of the reference spots associated with the measurement spots or sequence signals or sequence data obtained therefrom to form combination signals or combination sequence signals or combination sequence data corresponding to summary or average measuring and reference signals or measuring and reference sequence signals or measuring and reference sequence data and differences or ratios between the optionally standardized measuring combination signals or measuring combination sequence signals or measuring combination sequence data, and the optionally standardized reference combination signals or reference combination sequence signals or reference combination sequence data, in order to obtain information about the variable to be measured or the change therein.

2. The sensor means as claimed in claim 1, wherein the spots are arranged in a distributed manner such that relative to at least one further direction measurement spots responding to the same variable to be measured are arranged between associated reference spots, and reference spots are arranged between associated measurement spots responding to the same variable.

3. The sensor means as claimed in claim 1, wherein the sensor spots are configured so as to be extended relative to a further direction and in this further direction measurement spots responding to the same variable and associated reference spots extend next to one another and if appropriate are not offset from one another.

4. The sensor means as claimed in claim 1, wherein the group of measurement spots comprises at least four, preferably at least eight, most preferably at least twelve, more preferably still at least twenty measurement spots which respond to the same variable and are distributed with the associated reference spots over the common arrangement region such that such measurement spots are arranged between reference spots, and reference spots are arranged between such measurement spots relative to the at least one direction.

5. The sensor means as claimed in claim 1, wherein relative to the at least one direction for a plurality of measurement spots, preferably at least four measurement spots, responding to the same variable to be measured and for a plurality of associated reference spots, preferably at least four reference spots, measurement spots and reference spots which are immediately adjacent to one another have a spacing of at most 3,000 μm, preferably a spacing of at most 300 μm, or abut one another with an imperceptible or almost imperceptible spacing.

6. The sensor means as claimed in claim 1, wherein each group of a plurality of first groups of sensor spots of the arrangement is configured as measurement spots, each of the measurement spots of a group responding to at least one same variable to be measured and the measurement spots of a plurality of different groups responding to various variables to be measured.

7. The sensor means as claimed in claim 6, wherein a second group of sensor spots of the arrangement, which is configured as reference spots, is jointly associated with the groups of measurement spots and wherein the measurement spots of the groups of measurement spots and the reference spots of the group of reference spots are distributed over a common arrangement region.

8. The sensor means as claimed in the claim 6, wherein each group of measurement spots is associated with its own second group of sensor spots of the arrangement, which is configured as reference spots and wherein for each group of measurement spots and the associated group of reference spots its respective own common arrangement region is provided, over which the measurement spots of the group of measurement spots and the reference spots of the associated group of reference spots are distributed and which is offset from the common arrangement region or regions of other groups of measurement and reference spots.

9. The sensor means as claimed in claims 8, wherein the measurement spots of each group of measurement spots and the reference spots of the group associated therewith of reference spots are each distributed over the respective common arrangement region in such a way that relative to at least one direction the measurement spots are arranged between reference spots, and reference spots are arranged between measurement spots.

10. The sensor means as claimed in claim 9, wherein the measurement spots of each group of measurement spots and the reference spots of the group associated therewith of reference spots are each arranged in the respective common arrangement region.

11. The sensor means as claimed in claim 1, wherein at least four, preferably at least eight, most preferably at least twelve, more preferably still at least twenty different groups of measurement spots are provided.

12. The sensor means as claimed in claim 1, wherein the sensor spots or a plurality of the sensor spots are arranged distributed on a preferably planar surface and preferably form at least one two-dimensional field of sensor spots that corresponds to a common arrangement region.

13. The sensor means as claimed in claim 12, wherein the sensor spots arranged on the surface are sheet-like in their configuration.

14. The sensor means as claimed in claim 1, wherein the sensor spots or a plurality of the sensor spots are arranged distributed in a volume and preferably form at least one three-dimensional field of sensor spots that corresponds to a common arrangement region.

15. The sensor means as claimed in claim 1, wherein the measurement spots of each group are functionalized for at least one specific molecule or at least one molecule of a specific group of molecules to bind thereto and wherein the measuring signal represents the binding of at least one such molecule to a respective measurement spot or the amount of or a volume taken up by such molecules bound to a respective measurement spot as a variable to be measured.

16. The sensor means as claimed in claim 1, wherein the measurement spots of each group are functionalized for at least one specific biological object or object fragment or at least one biological object or object fragment of a specific group of biological objects or object fragments to bind thereto and wherein the measuring signal represents the binding of at least one such object or object fragment to a respective measurement spot or the amount of or a volume taken up by such objects or object fragments bound to a respective measurement spot as a variable to be measured.

17. The sensor means as claimed in claim 1, wherein the plasmon resonance, including a surface plasmon resonance, is excitable in the substrate by preferably optical means and wherein the measuring signal and the reference signal are dependent on the excitation or non-excitation of a plasmon resonance or surface plasmon resonance or on the interaction of the excited plasmons or surface plasmons with the environment in the region of a respective measurement spot or reference spot.

18. The sensor means as claimed in claim 1, wherein the measuring assembly is adapted for providing the measuring and reference signals.

19. The sensor means as claimed in claim 18, wherein the measuring and reference signals are provided by the measuring assembly based on at least one of optical and electrical interactions with the sensor spots.

20. The sensor means as claimed in claim 19, wherein the measuring assembly is configured to detect optical signals representing optical interaction between supplied electromagnetic radiation and at least one of the sensor spots and the environment thereof or a change in the optical interaction and to provide electrical signals or digital data representing the interaction or change in the interaction.

21. The sensor means as claimed in claim 20, wherein the measuring assembly comprises an image detection means, preferably a CCD or CMOS camera, or a detector field or detector array for detecting the optical signals.

22. The sensor means as claimed in claim 18, wherein the measuring assembly is configured to provide individual measuring signals or reference signals for the measurement spots and reference spots.

23. The sensor means as claimed in claim 1 being configured as a surface plasmon resonance measuring means.

24. The sensor means as claimed in claim 1 being configured as a chemosensor or biosensor means.

25. The sensor means as claimed in claim 1, wherein the boundary condition variable is a variable from the group consisting of temperature, pressure, index of refraction, concentration, density and electrical potential.

26. The sensor means as claimed in claim 1, wherein sensor spots which serve as reference spots and are optionally functionalized for this purpose serve as measurement spots, in particular are functionalized for this purpose, relative to at least one other variable to be measured.

27. The sensor means as claimed in claim 1, wherein sensor spots which serve as measurement spots and in particular are functionalized for this purpose serve as reference spots relative to at least one other variable to be measured and optionally are functionalized for this purpose.

28. A measuring process, carried out using a sensor means as claimed in claim 1.

* * * * *